United States Patent
Pegard et al.

(10) Patent No.: US 11,654,101 B2
(45) Date of Patent: May 23, 2023

(54) USE OF MAGNOLIA, JUNIPER OR VIOLET ABSOLUTE IN COSMETICS FOR DEPIGMENTING THE SKIN

(71) Applicant: ROBERTET S.A., Grasee (FR)

(72) Inventors: Anthony Pegard, Grasse (FR); Karine Kormann, Valbonne (FR)

(73) Assignee: ROBERTET S.A., Grasse (FR)

( * ) Notice: Subject to any disclaimer, the term of this patent is extended or adjusted under 35 U.S.C. 154(b) by 125 days.

(21) Appl. No.: 16/764,564

(22) PCT Filed: Dec. 20, 2018

(86) PCT No.: PCT/FR2018/053455
§ 371 (c)(1),
(2) Date: May 15, 2020

(87) PCT Pub. No.: WO2019/122748
PCT Pub. Date: Jun. 27, 2019

(65) Prior Publication Data
US 2020/0281846 A1    Sep. 10, 2020

(30) Foreign Application Priority Data
Dec. 21, 2017 (FR) ..................... 17/62760

(51) Int. Cl.
    *A61K 8/9789*     (2017.01)
    *A61K 8/9767*     (2017.01)
    *A61Q 19/02*     (2006.01)

(52) U.S. Cl.
CPC .......... *A61K 8/9789* (2017.08); *A61K 8/9767* (2017.08); *A61Q 19/02* (2013.01)

(58) Field of Classification Search
None
See application file for complete search history.

(56) References Cited

U.S. PATENT DOCUMENTS

| 2010/0209407 A1* | 8/2010 | Pain ........................ A61K 36/28 |
| | | 424/93.51 |
| 2012/0213719 A1 | 8/2012 | Kang et al. |
| 2014/0323950 A1* | 10/2014 | Wirth .................. A61K 8/9717 |
| | | 604/20 |
| 2017/0224757 A1* | 8/2017 | Huber ................... A61K 36/31 |

FOREIGN PATENT DOCUMENTS

| CN | 105832583 A | 8/2016 |
| JP | 2001-48773 A | 2/2001 |
| JP | 2002-003336 A | 1/2002 |
| JP | 2012-171960 A | 9/2012 |
| JP | 2013-166713 A | 8/2013 |
| KR | 10-2008-0104760 A | 12/2008 |
| KR | 101179589 B1 * | 9/2012 |
| KR | 101179589 B1 | 9/2012 |

OTHER PUBLICATIONS

Girard L. "État Actuel De La Question Des Concretes et Des Absolues De Concrètes" Industries De La Parfumerie, vol. 2, Jan. 1, 1947, pp. 183-262.
Mar. 22, 2019 International Search Report issued in International Patent Application No. PCT/FR2018/053455.

* cited by examiner

*Primary Examiner* — H. Sarah Park
(74) *Attorney, Agent, or Firm* — Oliff PLC

(57) ABSTRACT

The cosmetic use of one or more absolute(s) obtained from *magnolia*, juniper or violet for depigmenting the skin.

8 Claims, 1 Drawing Sheet

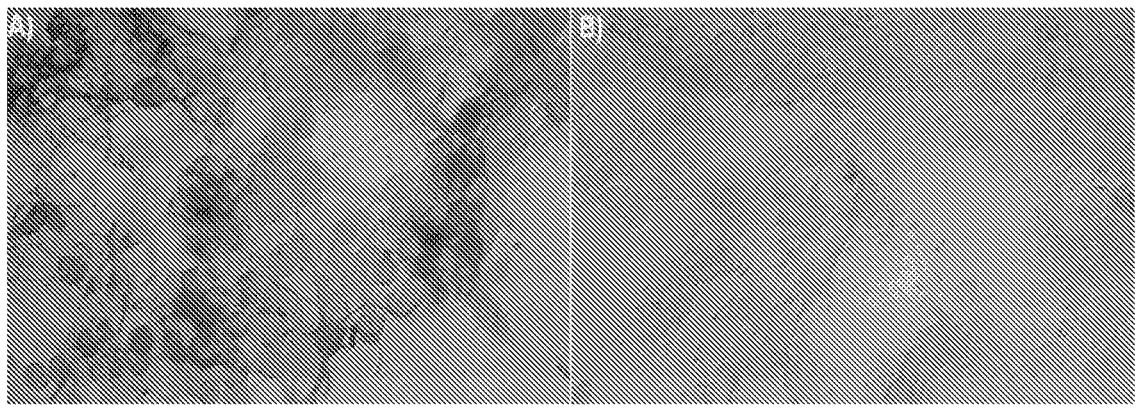
*Murine cells B16-F10 : controls (A) and incubated with the mixture according to the invention (B).*

USE OF MAGNOLIA, JUNIPER OR VIOLET ABSOLUTE IN COSMETICS FOR DEPIGMENTING THE SKIN

The present invention relates to the cosmetic use of one or several absolute(s) obtained from *magnolia*, juniper or violet to depigment the skin.

The pigmentation of the skin essentially results from the contents thereof in melanic pigments. Melanin is produced in the melanocytes at the basis of the epidermis, and then transferred to the keratinocytes to reach the top layers of the epidermis.

The key enzyme in the first one of the two steps of the melanogenesis is tyrosinase (monophenol, L-dihydroxyphenylalanine (L-DOPA): oxygen oxido-reductase EC 1.14.18.1). It enables the hydroxylation of the L-tyrosine into L-DOPA (o-diphenol product) and which is oxidized afterwards into dopaquinone.

Although regulated by intrinsic (hormones, transcription factors), and extrinsic (UV) factors, disruptions of the melanogenesis may occur. Then, there appear losses of the pigmentation (leukodermas, oculocutaneous albinism) or on the contrary hyperpigmentations with chloasma (pregnancy mask) or lentigos (age spots).

In order to correct these aesthetically unpleasant hyperpigmentations, numerous studies have been conducted in order to find lightening compounds: melano-toxic substances, inhibitors of the transfer of melanin to the keratinocytes, tyrosinase inhibitors. However, the compounds that have been found have turned to be harmful: allergenic, mutagenic, carcinogenic and reprotoxic. This is for example the case of the kojic acid, a tyrosinase inhibitor by copper chelation, used as a depigmenting substance. Controversial, its prohibition, already applied in Japan, is currently discussed in Europe.

The purified enzyme of the *Agaricus bisporus* fungus is commonly used but might sometimes result in very different results in comparison with the human tyrosinase.

In the context of the search for cosmetic active substances allowing depigmenting the skin, it is therefore interesting to identify products allowing inhibiting the melanogenesis by inhibiting the tyrosinase which induces the synthesis of melanin from tyrosine, but featuring none of the aforementioned defects.

The cosmetic use of some vegetal extracts, in particular of extracts of *Magnolia* barks, and more particularly of *Magnolia sieboldii* or of *Magnolia officinalis*, to whiten the skin is known. The vegetal extracts used in cosmetics are conventionally obtained by extraction with polar solvents, in order to obtain the molecules that have affinity to water. In particular, the essential oils are generally obtained by steam distillation.

The absolute is an extract, generally obtained from a vegetal material, widely used in the perfume industry. In contrast with plant extracts that are commonly used in cosmetics, the absolute is obtained by alcoholic transformation of one concrete, which is itself obtained by extraction with a volatile organic solvent. The absolutes may contain molecules that are different from those contained in the usual cosmetic plant extracts. More specifically, the absolute is obtained from a concrete, which is generally prepared by maceration of a fresh plant (flowers, roots, leaves, barks, berries, etc.) in a hydrocarbon volatile organic solvent such as hexane or petroleum ether, or a bi-solvent mixture such as hexane/ethyl acetate, hexane/isopropyl acetate, hexane/isopropyl alcohol, cyclohexane/ethyl acetate, cyclohexane/isopropyl acetate, or cyclohexane/isopropyl alcohol, or mixtures of linear or C6 cyclic hydrocarbons with the ethyl acetate, the isopropyl acetate or the isopropyl alcohol; in $CO_2$ in the supercritical state; or in a liquefied gas (or a mixture of liquefied gases) such as butane or 1,1,1,2-tetrafluoroethane (HFC-134a). Afterwards, the solvent is evaporated so as to produce a paste called concrete which contains aromatic compounds, waxes and oily compounds of the plant.

The concrete, which contains waxes which are responsible for the turbidity of the solution and make the latter sparingly soluble in the base of the perfume, cannot be used in alcoholic perfumery as such but can be used in soaps.

Hence, the elimination, at least partial, of the waxes is necessary. This elimination is achieved by frosting and filtration: after addition of alcohol to the concrete, the obtained alcoholic solution is homogenized under strong stirring at a temperature of about 30° C. to 60° C. and then refrigerated between −5° C. and −18° C. so that the ex-concrete waxes could be eliminated by precipitation and filtration. Afterwards, the alcohol is evaporated to obtain the absolute.

Thus, the use of absolutes of *magnolia*, juniper or violet in perfumery is known. Nevertheless, the use of these absolutes in cosmetics, in particular to depigment the skin, has never been reported or suggested.

Yet, surprisingly, it has now been found that an absolute obtained from *magnolia*, juniper or violet has particularly interesting tyrosinase inhibitory properties, which enables its cosmetic use to depigment the skin (or for whitening the skin).

Thus, an object of the present invention is the cosmetic use of one or several absolute(s) obtained from *magnolia*, juniper or violet to depigment the skin.

BRIEF DESCRIPTION OF THE DRAWING

FIG. 1 shows photographs of control murine B16-F10 cells (A), and murine B16-F10 cells incubated with a mixture *Magnolia* Absolute/Juniper Absolute/Violet Absolute (B).

In the context of the present invention, by «absolute», it should be understood any extract of a vegetal material, which can be obtained by any method known to those skilled in the art (cf. for example: Girard L: «Etat actuel de la question des concrètes et des absolues de concretes», Industries de la parfumerie, Vol. 2, Jan. 1, 1947, pages 183-262), and in particular by the following method:

preparation of a concrete in a pasty form
by maceration of the fresh vegetal material in a hydrocarbon volatile organic solvent such as hexane or petroleum ether, or a bi-solvent mixture such as hexane/ethyl acetate, hexane/isopropyl acetate, hexane/isopropyl alcohol, cyclohexane/ethyl acetate, cyclohexane/isopropyl acetate, or cyclohexane/isopropyl alcohol, or mixtures of linear or C6 cyclic hydrocarbons with the ethyl acetate, the isopropyl acetate or the isopropyl alcohol; in $CO_2$ in the supercritical state; or in a liquefied gas (or a mixture of liquefied gases) such as butane or HFC134a;

followed by the evaporation of the solvent or the solvent mixture;

elimination, at least partial, of the waxes contained in the concrete thus obtained so as to obtain the absolute by addition of alcohol;

homogenization of the solution thus obtained by strong stirring at a temperature of about 30° C. to 60° C.;

refrigeration of the solution between −5° C. and −18° C. and elimination of the ex-concrete waxes by precipitation and filtration;

and evaporation of the alcohol.

The method for producing the absolute may be followed, where needed, with a step of purifying the absolute by any technique known to those skilled in the art, in particular through molecular distillations or by using ion-exchange resins.

The absolutes may be obtained from any portions of the considered plant, such as for example the bud, the cone, the needles, the flower, the root, the sap, the bark, the berry, the stem or the leaf.

In addition, in the context of the present invention:

by «*magnolia*», it should be understood any *magnolia* species, and in particular the *Magnolia officinalis* species;

by «juniper», it should be understood any juniper species, and in particular the *Juniperus communis* species;

by «violet», it should be understood any violet species, and in particular the *Viola odorata* species;

by «cosmetic use to depigment the skin», it should be understood any non-therapeutic use of a product for obtaining a lightening and/or homogenization of the tone of the skin.

Finally, in the context of the present invention, and unless otherwise indicated, the proportions expressed in % correspond to weight percentages with respect to the overall weight of the considered entity.

Hence, an object of the present invention is a use of one or several absolute(s) obtained from *magnolia*, juniper or violet to depigment the skin.

Preferably, said absolute(s) has/have all or part of the following features:

the absolute obtained from *magnolia* is obtained from the *magnolia* bark; more preferably from the *Magnolia officinalis* bark;

the absolute obtained from juniper is obtained from the juniper berry; more preferably from the *Juniperus communis* berries; and/or the absolute obtained from violet is obtained from the violet leaves; more preferably from the *Viola odorata* leaves.

Also preferably, the absolutes used in the context of the present invention have been obtained from a concrete which has itself been obtained by extraction with hexane.

In the context of the present invention, the aforementioned absolutes may be used alone or in combination. Yet, a synergy of action has been observed when several ones of the aforementioned absolutes are combined. Thus, a preferred object of the present invention is the cosmetic use of one of the following combinations of absolutes to depigment the skin:

the absolute obtained from *magnolia* as previously defined and the absolute obtained from juniper as previously defined;

the absolute obtained from *magnolia* as previously defined and the absolute obtained from violet as previously defined;

the absolute obtained from juniper as previously defined and the absolute obtained from violet as previously defined; or the absolute obtained from *magnolia* as previously defined, the absolute obtained from juniper as previously defined; and the absolute obtained from violet.

Hence, the absolutes described in the context of the present invention are used in cosmetics for their depigmenting effect. For this purpose, these absolutes may be incorporated in a cosmetic composition which may be formulated in any galenic form suitable for the administration thereof, in particular for the application thereof on the skin (topically).

The cosmetic compositions comprising the extract used in the context of the present invention may be formulated in the liquid, pasty, or solid form, and more particularly in the form of ointments, creams, milks, pomades, powders, soaked swabs (towelettes), solutions, gels, sprays, foams, suspensions or sticks. It may also be in the form of suspensions of microspheres or nanospheres, of lipid or polymeric vesicles or of polymeric or gelled patches allowing for a controlled release, but also in the form of rinse-off products such as shower gels, bathing products (salts, lather, etc.).

These cosmetic compositions contain the absolute (or the absolutes) used in the context of the present invention at contents ranging from 0.0001% to 10% with respect to the overall weight of the composition, preferably from 0.001% to 1% with respect to the overall weight of the composition.

For the preparation of these compositions, the absolute used in the context of the present invention is mixed with excipients that are conventionally used in the cosmetics field.

The compositions comprising the absolute (or the absolutes) used in the context of the present invention may be in the form of perfuming compositions having a cosmetic activity, such as for example the compositions of the Actiscent® range.

The cosmetic compositions comprising the absolute (or the absolutes) used in the context of the present invention may be in the form of a cream in which said fraction is associated with the excipients that are commonly used in cosmetology.

These compositions may also be in the form of gels in the suitable excipients such as cellulose esters or other gelling agents, such as carbopol, sepinov (polyacrylate) or guar gum.

These compositions may also be in the form of a lotion or a solution in which the extract used in the context of the present invention is in the encapsulated form. For example, the microspheres may be constituted by fats, agar and water. The extract used in the context of the present invention may be incorporated into vectors such as liposomes, glycospheres, cyclodextrins, in chylomicrons, macro-, micro-, nano-particles as well as macro-, micro- and nano-capsules and also be absorbed on powdery organic polymers, talcs, bentonites and other mineral supports.

These emulsions have a good stability and can be preserved as long as necessary for use at temperatures comprised between 0 and 50° C. without any sedimentation of the constituents or separation of the phases.

The cosmetic compositions comprising the absolute (or the absolutes) used in the context of the present invention may also contain additives or adjuvants that are common in cosmetology, such as for example antimicrobial substances or perfumes but also extracted or synthetic lipids, gelling and viscosifying polymers, surfactants and emulsifiers, water- or fat-soluble active substances, extracts of plants, tissue extracts, marine extracts, synthetic active substances.

The cosmetic compositions comprising the absolute (or the absolutes) used in the context of the present invention may also comprise other complementary active substances selected for their action, for example for the slimming effect, the anti-cellulite effect, the firming effect, the moisturizing effect, the anti-ageing effect, the anti-microbial activity, the anti-oxidative activity, the anti-radicalizing activity, the healing effect, the tightening effect, the anti-wrinkle effect, the chelating activity, the complexing and sequestering activity, the soothing effect, the anti-dark circles effect, the anti-redness effect, the emollient activity, the capillary disentangling effect, the anti-dandruff activity, the hair regrowth simulating effect, the hair loss inhibiting effect, the capillary sheathing effect, the depilatory activity, the hair regrowth limiting activity, the cell renewal promoting activity, the inflammatory response modulating activity, the facial oval maintenance activity, but also for sun protection, the anti-irritating activity, cellular nutrition, cellular respiration, anti-seborrheic treatments, cutaneous tonicity, hair protection.

When the cosmetic compositions comprising the extract used in the context of the present invention contain complementary active substances, these are generally present in the composition at a concentration that is high enough so these could exert their activity.

The cosmetic compositions comprising the absolute (or the absolutes) used in the context of the present invention are preferably used on a daily basis and applied once or several times a day. They may be applied over all areas requiring a reduction of the pigmentation, in particular over the face, the skull, the legs, the hands, the torso, the arms or the back.

Finally, in another aspect, another object of the present invention is a method to reduce the pigmentation of the skin comprising the selection of a skin area over which the reduction of the pigmentation is looked for, and the application on said area of at least one absolute selected from the absolutes obtained from *magnolia*, juniper or violet as previously defined in a sufficient amount to reduce said pigmentation.

The present invention is illustrated in a non-limiting manner by the following examples.

EXAMPLE 1—EFFECTIVENESS IN VIVO OF THE COMPOSITIONS OF THE INVENTION

Preparation of the *Magnolia* Absolutes

In a 20 liter reactor, 3 kg of crushed *Magnolia* barks are extracted with 5 volumes of hexane at ambient temperature and under mechanical stirring for 1 h30. The whole is left to settle for 30 minutes and then filtered on a pleated filter. The exhausted barks are extracted again with 5 volumes of hexane under the same conditions as previously described.

The two extraction filtrates are combined together and vacuum concentrated in the rotary evaporator (40° C. under 30 mbar).

186.3 g of a green-brown viscous liquid (concrete) are obtained, that is to say a 6.2% yield.

In a 4 liter reactor provided with a mechanical stirring, the concrete thus obtained (186.3 g) is dissolved in 6 volumes of denatured alcohol and stirred for 1 h at 45° C.

Then, the whole is left to ice over in the freezer for 12 hours.

The solution is filtered on a sinter provided with a Celite bed. Thus, a first filtrate (S1) is collected.

The residual waxes retained on the sinter are washed again with 2 volumes of cold denatured alcohol. Thus, a second filtrate (S2) is collected.

The two filtrates are vacuum concentrated separately in the rotary evaporator (50° C. under 30 mbar). A solubility test is performed on the two concentrated filtrates individually to check up that they have no insoluble matter when they are put in solution at 10% in the alcohol.

The two concentrated filtrates are then mixed and 114.3 g of an orange-brown liquid is obtained, that is to say a 61.3% yield (*Magnolia* absolute).

Preparation of the Juniper and Violet Absolutes

The method described hereinbefore has also allowed obtaining the following absolutes:

«Juniper absolute» corresponding to the absolute obtained from *Juniperus communis* berries; and «Violet absolute» obtained from *Viola odorata* leaves.

EXPERIMENTAL PROTOCOL

The following protocol has allowed determining the half-maximal inhibitory concentration (IC50) of the different absolutes, alone or in combination. The $IC_{50}$ is a measurement of the effectiveness of a given compound to inhibit a specific biological or biochemical function. In this instance, IC50 corresponds to the concentration at which the ratio for the maximum rate of transformation of the substrate into product for the condition on the Vmax of the transformation for the control is 50%.

In vivo model tests on melanin-producing cells, the murine melanocytes B16-F10, have been necessary. The decrease in the cellular tyrosinase activity, associated with a reduction of the intracellular melanin content, while preserving the survival of the cells by non-cytotoxic concentrations, have then been investigated. For this purpose, the B16-F10 cells have been seeded into 24-well plates, and incubated for 24 h at 37° C. with several concentrations of different selected raw materials. The kojic acid has also been used as reference product. Afterwards, the cells are lysed, and centrifuged.

The supernatant contains tyrosinase that is deposited in a 96-well plate and to which L-DOPA substrate is added, and then the absorbance at 490 nm is read every 10 min for 1 hour. The maximum rate of the condition/maximum rate of the negative control ratio, gives the inhibition rate of the condition and allows estimating the IC50 of each raw material.

In turn, the cell pellet is dissolved by a NaOH 1N solution and incubated for 1 hour at 70° C. before being deposited in a 96-well plate put in the spectrophotometer at 405 nm. Afterwards, a comparison with the absorbance of a standard melanin calibrated range allows determining the intracellular melanin content of each condition and checking on the inhibitor effect of the melanogenesis by the different raw materials.

A cell viability test in tetrazolium MTT salt (3-(4,5-dimethylthiazol-2-yl)-2,5-diphenyl tetrazolium bromide) is performed. For this purpose, the cells are incubated at 37° C. for 3 h in a medium containing 1 mg/ml of MTT, before solubilizing the formed formazan crystals by the DMSO and reading the absorbance at 570 nm. The cell survival rate is expressed in percentage with respect to the negative controls.

Results

The obtained results are reported in the following Tables 1 and 2, as well as in FIG. 1 representing photographs of control murine cells B16-F10 (A) and incubated with the mixture *Magnolia* Absolute/Juniper Absolute/Violet Absolute (1/1/1) (B).

TABLE 1

Tests on B16 melanocytes, with the assessment of the activity of the intracellular tyrosinase

| Ingredient | Effective IC50 (ppm) | Theoretical IC50 |
|---|---|---|
| Magnolia Absolute | 18 | — |
| Juniper Absolute | 9 | — |
| Violet Absolute | 17 | — |
| Magnolia Absolute/Juniper Absolute (1/1) | 7 | 12 |
| Magnolia Absolute/Violet Absolute (1/1) | 10 | 17 |
| Violet Absolute/Juniper Absolute (1/1) | 4 | 13 |
| Magnolia Absolute/Juniper Absolute/ Violet Absolute (1/1/1) | 4.2 | 13 |
| Kojic acid | 225 | — |

TABLE 2

Tests on B16 melanocytes, with dosing of the intracellular melanin.

| Ingredient | Effective IC50 (ppm) | Theoretical IC50 |
|---|---|---|
| Magnolia Absolute | 18.5 | — |
| Juniper Absolute | 111 | — |
| Violet Absolute | 54 | — |
| Magnolia Absolute/Juniper Absolute (1/1) | 20 | 32 |
| Magnolia Absolute/Violet Absolute (1/1) | 18 | 28 |
| Violet Absolute/Juniper Absolute (1/1) | 52 | 73 |
| Magnolia Absolute/Juniper Absolute/ Violet Absolute (1/1/1) | 21 | 37 |
| Kojic acid | 214 | — |

CONCLUSION

The obtained results confirm the inhibitory activity of tyrosinase and of the synthesis of the intracellular melanin of each of the tested absolutes, and therefore their cosmetic effectiveness in depigmenting the skin.

Furthermore, these results highlight the existence of an unexpected synergy of action between the different absolutes. This synergy is observed for the combinations of two or three absolutes.

The invention claimed is:

1. A cosmetic method comprising:
    applying two or more absolutes to depigment the skin, the two or more absolutes comprising:
        a *magnolia* absolute obtained from a vegetal material of the *magnolia* by alcoholic extraction of a *magnolia* concrete; and
        a juniper extract obtained from a vegetal material of the juniper by alcoholic extraction of a juniper concrete,
    wherein the *magnolia* and juniper concretes are each independently obtained by extraction with a volatile organic solvent that comprises at least one solvent selected from the group consisting of hexane, petroleum ether, cyclohexane, $CO_2$ in the supercritical state, butane, and 1,1,1,2-tetrafluoroethane (HFC-134a).

2. The method according to claim 1, wherein the *magnolia* and juniper absolutes are applied in an approximate mass ratio of 1:1.

3. A cosmetic method comprising:
    applying two or more absolutes to depigment the skin, the two or more absolutes comprising:
        a *magnolia* absolute obtained from a vegetal material of the *magnolia* by alcoholic extraction of a *magnolia* concrete; and
        a violet extract obtained from a vegetal material of the violet by alcoholic extraction of a violet concrete,
    wherein the *magnolia* and violet concretes are each independently obtained by extraction with a volatile organic solvent that comprises at least one solvent selected from the group consisting of hexane, petroleum ether, cyclohexane, $CO_2$ in the supercritical state, butane, and 1,1,1,2-tetrafluoroethane (HFC-134a).

4. The method according to claim 3, wherein the *magnolia* and violet absolutes are applied in an approximate mass ratio of 1:1.

5. A cosmetic method comprising:
    applying two or more absolutes to depigment the skin, the two or more absolutes comprising:
        a juniper absolute obtained from a vegetal material of the juniper by alcoholic extraction of a *magnolia* concrete; and
        a violet extract obtained from a vegetal material of the violet by alcoholic extraction of a violet concrete,
    wherein the juniper and violet concretes are each independently obtained by extraction with a volatile organic solvent that comprises at least one solvent selected from the group consisting of hexane, petroleum ether, cyclohexane, $CO_2$ in the supercritical state, butane, and 1,1,1,2-tetrafluoroethane (HFC-134a).

6. The method according to claim 5, wherein the juniper and violet absolutes are applied in an approximate mass ratio of 1:1.

7. The method according to claim 5, wherein the two or more absolutes further comprises a *magnolia* absolute obtained from a vegetal material of the *magnolia* by alcoholic extraction of a *magnolia* concrete, which is itself obtained by extraction with a volatile organic solvent that comprises at least one solvent selected from the group consisting of hexane, petroleum ether, cyclohexane, $CO_2$ in the supercritical state, butane, and 1,1,1,2-tetrafluoroethane (HFC-134a).

8. The method according to claim 7, wherein the juniper, violet, and *magnolia* absolutes are applied in an approximate mass ratio of 1:1:1.

* * * * *